United States Patent [19]
Schaible

[11] Patent Number: 5,695,461
[45] Date of Patent: Dec. 9, 1997

[54] OPHTHALMIC INSTRUMENT FOR FRACTURING AND REMOVING A CATARACT AND A METHOD FOR USING THE SAME

[76] Inventor: Eric R. Schaible, 4382 Albacore Cir., Port Charlotte, Fla. 33948

[21] Appl. No.: 722,315

[22] Filed: Sep. 27, 1996

[51] Int. Cl.$^6$ ................................................... A61B 17/32
[52] U.S. Cl. .............................................. 604/22; 606/166
[58] Field of Search ............................. 604/22; 606/166, 606/170, 171, 180, 169

[56] References Cited

U.S. PATENT DOCUMENTS

| | | |
|---|---|---|
| 3,884,238 | 5/1975 | O'Malley et al. . |
| 3,908,661 | 9/1975 | Kramer . |
| 4,016,882 | 4/1977 | Broadwin et al. ............ 606/169 |
| 4,299,227 | 11/1981 | Lincoff . |
| 4,732,150 | 3/1988 | Keener, Jr. . |
| 4,908,015 | 3/1990 | Anis . |
| 5,057,098 | 10/1991 | Zelman . |
| 5,062,827 | 11/1991 | Wiksell ............ 604/22 |
| 5,232,451 | 8/1993 | Freitas et al. ............ 606/191 |
| 5,248,297 | 9/1993 | Takase ............ 604/22 |
| 5,318,011 | 6/1994 | Federman et al. . |
| 5,413,556 | 5/1995 | Whittingham . |

Primary Examiner—William Lewis
Attorney, Agent, or Firm—David P. Gordon

[57] ABSTRACT

A ophthalmic hand piece having a phaco needle or YAG laser is provided with a balloon nucleofractis irrigation sleeve. The balloon nucleofractis irrigation sleeve includes an irrigation conduit, a balloon fluid conduit, a balloon, and a connector for coupling the balloon nucleofractis irrigation sleeve to the distal end of the ophthalmic hand piece. The balloon fluid conduit is coupled adjacent to the irrigation conduit and the balloon is sealed to the distal end of the balloon fluid conduit. In practice, with the balloon contracted, the phaco needle or YAG laser is first used to carve a groove in the cataract. Once a groove has been carved, the balloon is positioned into the groove and swelled. Expansion of the balloon causes the cataract to fracture into halves or quarters. Each half or quarter can similarly be carved with a groove and fractured using swelling of the balloon. As the process is repeated, the pieces of the cataract are made smaller, and can be easily removed through standard phaco- or laser emulsification. In another embodiment, an ophthalmic instrument is provided with an irrigation sleeve fit with a fracture lever. Once a groove has been carved in a cataract, the phaco needle or tip of the YAG laser and a distal end of the fracture lever are inserted into the groove and are spread apart, thereby causing the cataract to fracture.

28 Claims, 5 Drawing Sheets

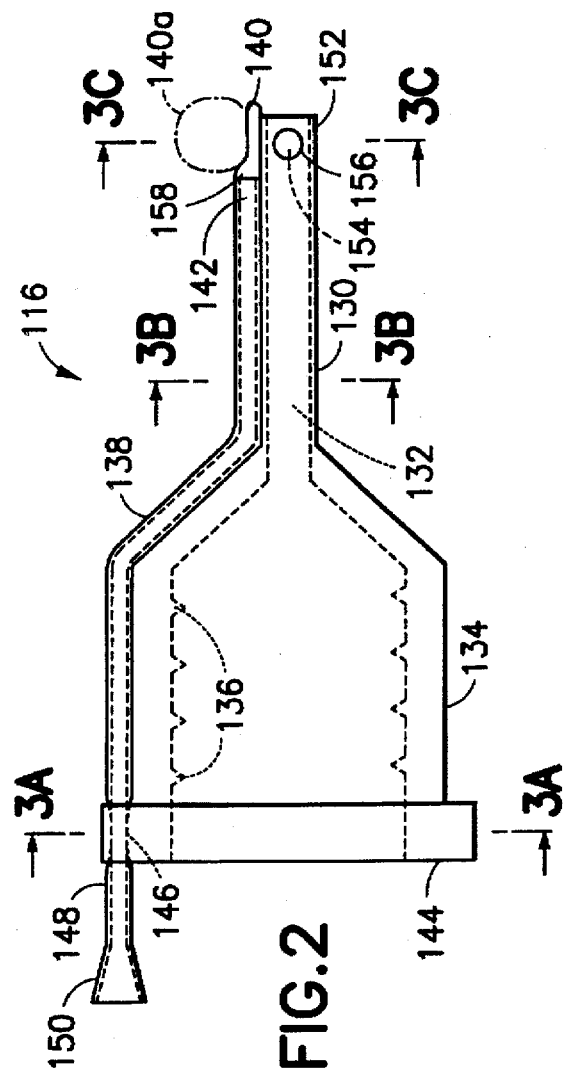
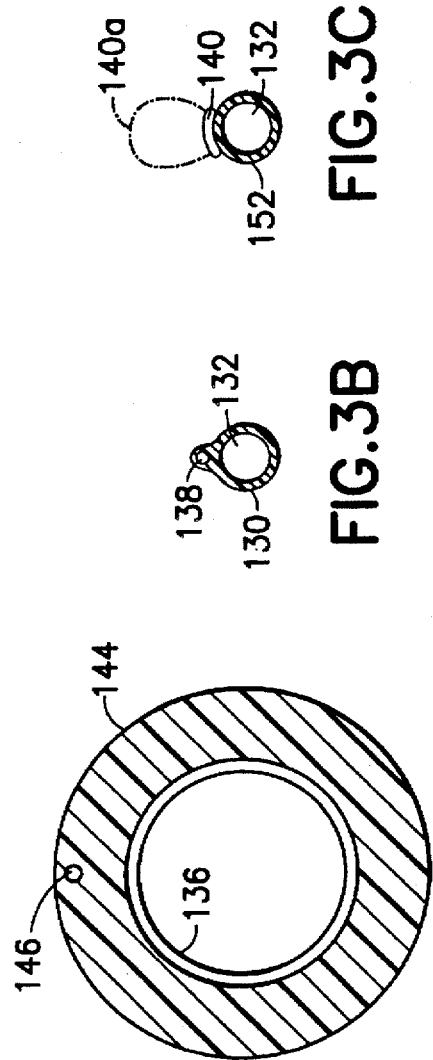

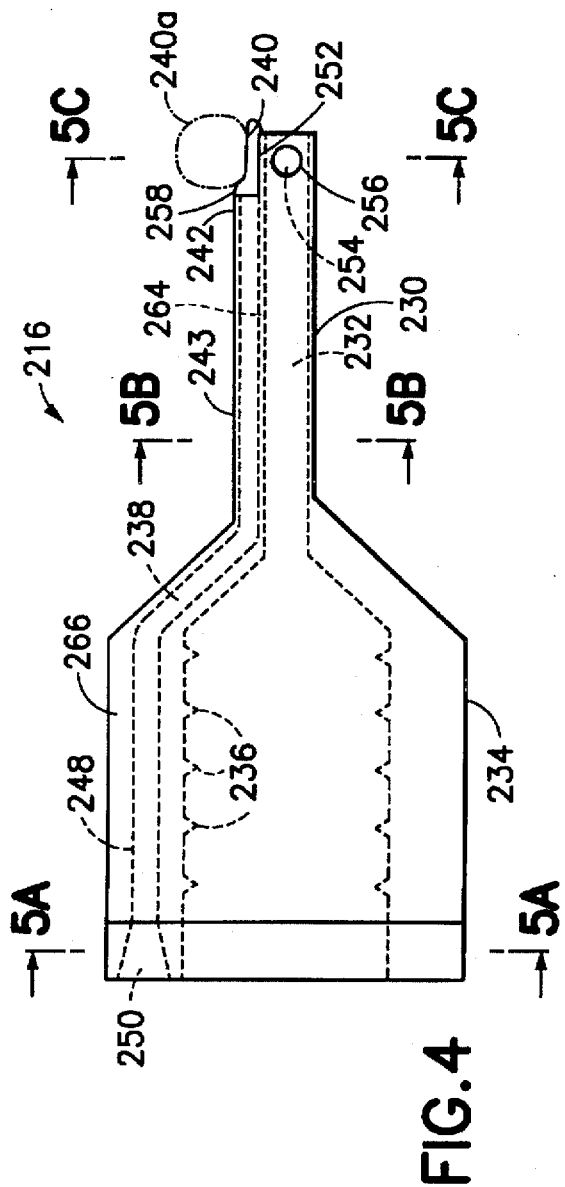
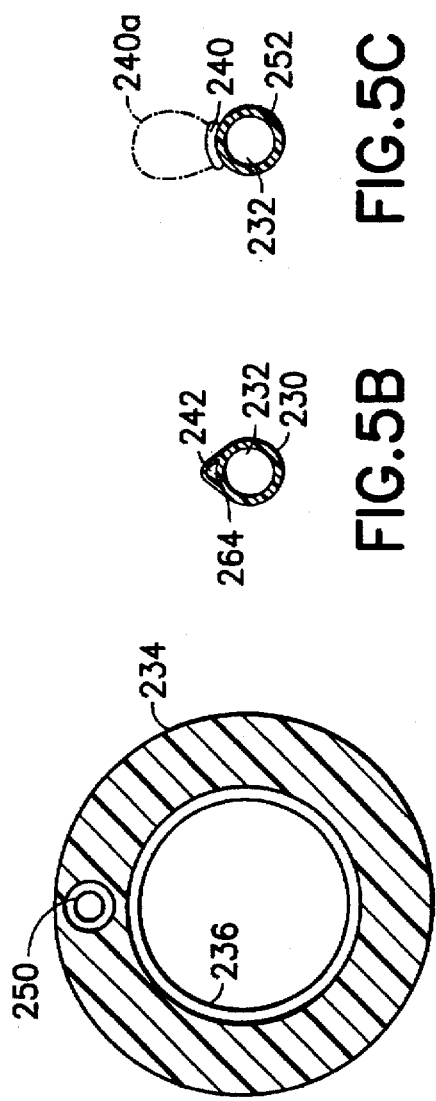

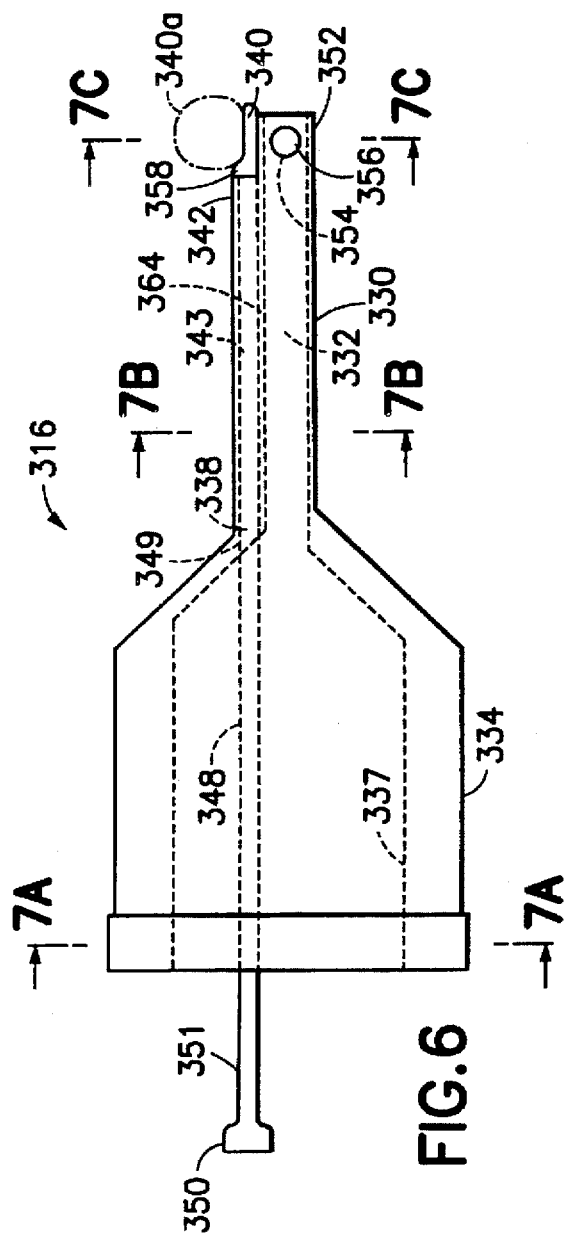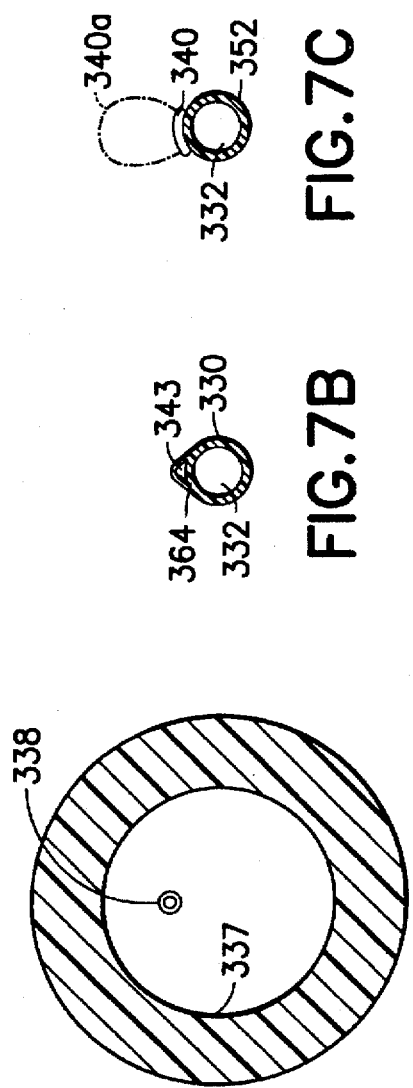

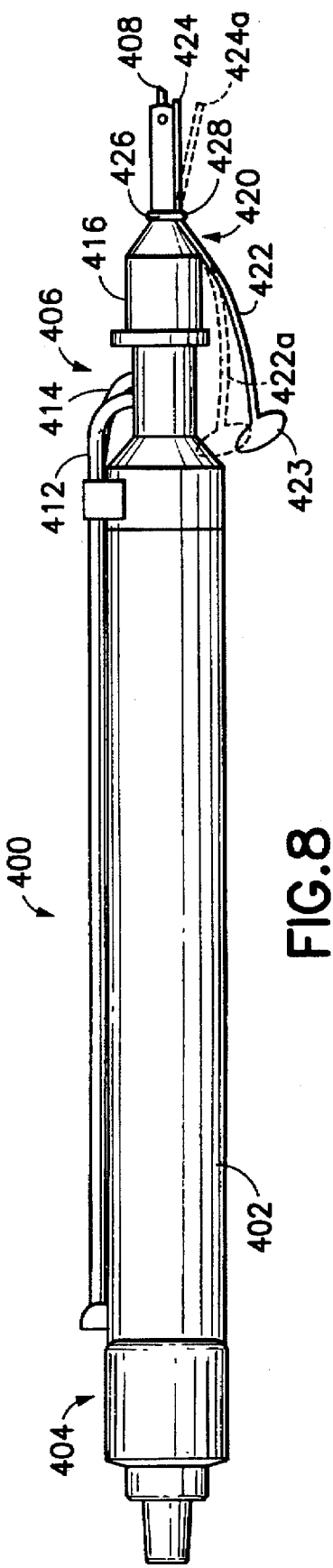
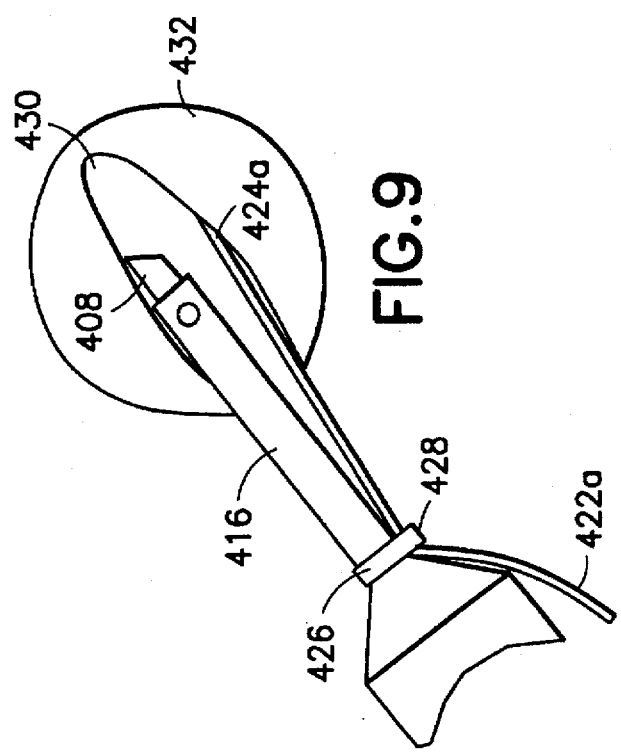
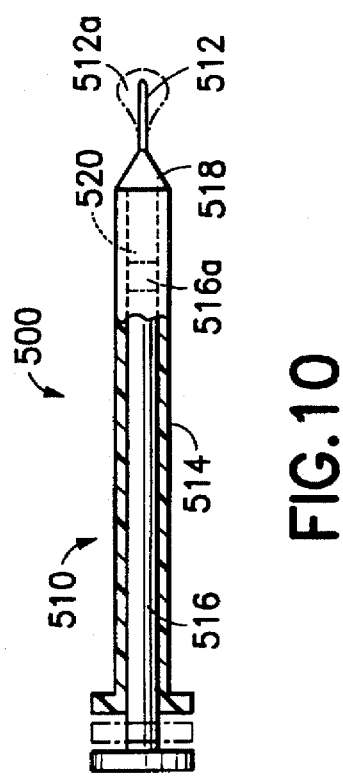

OPHTHALMIC INSTRUMENT FOR FRACTURING AND REMOVING A CATARACT AND A METHOD FOR USING THE SAME

BACKGROUND OF THE INVENTION

1. Field of the Invention

This invention relates broadly to ophthalmic instruments. More particularly, this invention relates to a nucleofractis apparatus for use with an ophthalmic hand piece during cataract surgery.

2. State of the Art

The human eye is divided into an anterior and posterior chamber by a normally transparent lens which focuses light onto the retina at the back of the posterior chamber. A cataract is an opacity of this normally transparent lens which obstructs vision. In order to restore vision, ophthalmic surgery is required to remove the cataract.

A number of techniques are used to surgically remove a cataract. One technique is to create a relatively large incision in the eye, to insert a surgical instrument through the incision, and to grip the cataract and pull it out through the incision. Such a large incision can traumatize the eye, resulting in an increased rate of post-surgical complications and post-operative astigmatism. As a result, this technique has fallen into disfavor.

More recently, phacoemulsification has been performed in which a phacoemulsification hand piece is used to emulsify and aspirate a cataract. The phacoemulsification hand piece generally includes a tubular housing manipulated by the practitioner, a fluid tube, an aspiration tube, a phaco needle and an irrigation sleeve extending over the distal end of the instrument such that the irrigation sleeve substantially covers the phaco needle. The phaco needle is a stainless steel cutting needle which vibrates ultrasonically at between 20 KHz and 40 KHz. The phaco needle is provided with a central aspiration conduit. A standard irrigation sleeve has an approximately 2.5 mm to 3.0 mm outer diameter distal portion and an approximately 9 mm outer diameter proximal base. The distal portion defines an irrigation conduit. The base has an internal opening approximately 5 mm in diameter and is usually provided with coupling means for coupling the irrigation sleeve to the distal end of the phacoemulsification hand piece. The irrigation sleeve is typically injection molded of a silastic material or other biocompatible material. The fluid tube is coupled to the irrigation conduit of the irrigation sleeve. The aspiration tube is coupled to the central aspiration conduit of the phaco needle.

In practice, the phaco needle is used through a relatively small 2.5 to 3 mm incision in the eye. The sharp phaco needle is then inserted into the lens at the location of the cataract and ultrasonically vibrates to carve away and emulsify the cataract. The emulsion is then aspirated out through the central aspiration conduit of the phaco needle and the aspiration tube. Fluid is irrigated into the eye from the fluid tube and through the irrigation conduit to maintain proper fluid pressure in the eye. However, emulsification of the cataract into small enough portions which can be aspirated through the phaco needle is very difficult. The cataract must be slowly shaved away until gone, requiring a relatively lengthy surgery and increasing the likelihood of complications. In addition, the tissues in the eye are very delicate. The vibrating sharp point of the phaco needle can inadvertently damage the delicate capsule of the lens.

Other techniques have attempted to more rapidly remove the cataract using multiple dedicated instruments for making an incision in the lens of the eye and for breaking apart the cataract. These techniques either require the practitioner to use both hands during cataract surgery, which is difficult, or to use one instrument to create a trough in the lens, another instrument to spread the trough and fracture the cataract, and a third instrument to remove the cataract. This requires more time and also requires more instruments to be inserted into and removed from the eye, which can cause trauma at the incision site.

SUMMARY OF THE INVENTION

It is therefore an object of the invention to provide a modified irrigation sleeve for an ophthalmic instrument hand piece which together will permit quick and efficient cataract removal.

It is another object of the invention to provide a modified irrigation sleeve for an ophthalmic instrument hand piece which will reduce the trauma to the eye of a patient undergoing cataract surgery.

It is a further object of the invention to provide a modified irrigation sleeve for an ophthalmic instrument hand piece which has a reduced likelihood of causing complications during cataract surgery.

It is an additional object of the invention to provide a modified irrigation sleeve which can be retrofit on standard ophthalmic instrument hand pieces.

In accord with these objects which will be discussed in detail below, an ophthalmic instrument hand piece having a phaco needle or YAG laser is provided with a modified irrigation sleeve, herein called a balloon nucleofractis irrigation sleeve. The balloon nucleofractis irrigation sleeve includes an irrigation conduit, a balloon fluid conduit, a balloon, and a connecting means for coupling the balloon nucleofractis irrigation sleeve to the distal end of the hand piece. The balloon fluid conduit is coupled adjacent to the irrigation conduit and the balloon is sealed fluidtight to the balloon fluid conduit. The balloon fluid conduit is also coupled to a balloon swelling means for swelling the balloon.

According to one embodiment of the invention, the balloon fluid conduit is injection molded along the periphery of the balloon nucleofractis irrigation sleeve. According to a second embodiment, the distal portion of the balloon fluid conduit is located along the periphery of the distal portion of the balloon nucleofractis irrigation sleeve and the proximal portion of the balloon fluid conduit is defined by a wall of the proximal portion of the balloon nucleofractis irrigation sleeve. According to a third embodiment, the distal portion of the balloon fluid conduit is located along the periphery of the distal portion of the balloon nucleofractis irrigation sleeve and the proximal portion of the balloon fluid conduit is a distinct flexible tube running through the inner diameter of the balloon nucleofractis irrigation sleeve.

In practice, with the balloon contracted, the phaco needle or YAG laser is first used to carve a groove in the cataract nucleus. Once a groove has been carved, the balloon is positioned into the groove and swelled with fluid. Swelling of the balloon causes the nucleus to fracture into halves or quarters. The balloon is then emptied. Each half or quarter can similarly be carved with a groove and fractured again by inserting and swelling the balloon. As the process is repeated, the pieces of the nucleus are made smaller, and can be easily removed through aspiration.

A fourth embodiment is also provided in which a lever having a proximal actuator arm and a distal end is coupled to an irrigation sleeve. In practice, a phaco needle or YAG laser is used to create a groove in the cataract. Then, the phaco needle or YAG laser and the distal end of the lever are inserted into the groove. When the practitioner presses the actuator arm with a finger to move the actuator arm radially inward, the distal end moves radially outward and splits the cataract.

A fifth embodiment is also provided in which a balloon nucleofractis apparatus is provided which is distinct from the ophthalmic hand piece.

Additional objects and advantages of the invention will become apparent to those skilled in the art upon reference to the detailed description taken in conjunction with the provided figures.

BRIEF DESCRIPTION OF THE DRAWINGS

FIG. 2 is a side elevation view of a balloon nucleofractis irrigation sleeve according to the invention;

FIG. 3A is a cross-sectional view across 3A—3A of FIG. 2;

FIG. 3B is a cross-sectional view across 3B—3B of FIG. 2;

FIG. 3C is a cross-sectional view across 3C—3C of FIG. 2;

FIG. 4 is a side elevation view of a balloon nucleofractis irrigation sleeve according to a second embodiment of the invention;

FIG. 5A is a cross-sectional view across 5A—5A of FIG. 4;

FIG. 5B is a cross-sectional view across 5B—5B of FIG. 4;

FIG. 5C is a cross-sectional view across 5C—5C of FIG. 4;

FIG. 6 is a side elevation view of a balloon nucleofractis irrigation sleeve according to a third embodiment of the invention;

FIG. 7A is a cross-sectional view across 7A—7A of FIG. 6;

FIG. 7B is a cross-sectional view across 7B—7B of FIG. 6;

FIG. 7C is a cross-sectional view across 7C—7C of FIG. 6;

FIG. 8 is a side elevational view of an ophthalmic instrument hand piece according to a fourth embodiment of the invention;

FIG. 9 is an enlarged broken perspective view of the embodiment of FIG. 8 in use; and FIG. 10 is a side elevation of a balloon nucleofractis instrument according to a fifth embodiment of the invention.

DETAILED DESCRIPTION OF THE PREFERRED EMBODIMENTS

Figure 1:
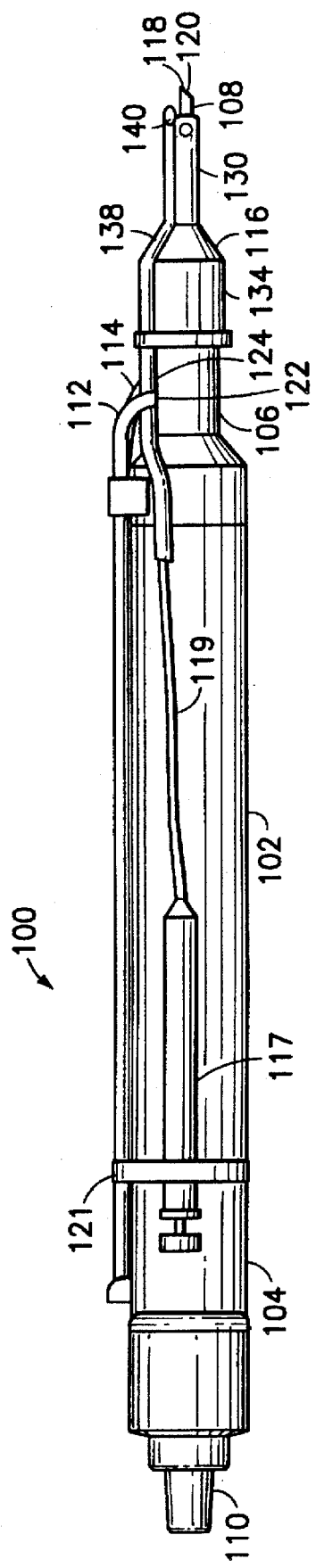
FIG. 1 is a side elevational view of an ophthalmic instrument hand piece according to the invention.

Turning now to FIG. 1, a phacoemulsification hand piece 100 is shown. The hand piece generally includes a tubular housing 102 having a proximal end 104 and a distal end 106, a phaco needle 108 attached to the distal end 106, a connector means 110 at the proximal end 104 for connecting a power supply for a piezoelectric motor (not shown) located within the housing 102 which vibrates the phaco needle, an external aspiration tube 112 and an external fluid tube 114. A balloon nucleofractis irrigation sleeve, or modified sleeve 116, extends over the phaco needle 108 and is coupled to the distal end 106 of the tubular housing. A syringe 117 is removably coupled by a strap 121 to the exterior of the housing 102 and is coupled to the modified sleeve 116 by a tube 119.

More particularly, the phaco needle 108 is a stainless steel needle which vibrates ultrasonically typically at between 20 KHz and 40 KHz by means of the piezoelectric motor. The phaco needle includes a sharp cutting tip 118 and a central aspiration conduit 120. The distal end of the housing includes an externally threaded portion (not shown) which couples to the modified sleeve 116, as described below with reference to FIGS. 2 and 3A. Proximal the threaded portion, the aspiration tube 112 enters through a first port 122 and is coupled to the central aspiration conduit 120 of the phaco needle 108, and the fluid tube 114 enters through a second port 124 and is coupled to the modified sleeve 116.

Referring to FIG. 2, the modified sleeve 116 is a hollow tubular member made from a biocompatible and relatively soft material, e.g., silicone or another silastic material. The modified sleeve 116 generally includes a narrow distal portion 130, a wide proximal portion 134, a balloon fluid conduit 138, and a balloon 140. Preferably, the modified sleeve 116 is injection molded to include the distal portion 130, the proximal portion 134, and the balloon fluid conduit 138 in one integral unit.

Referring to FIGS. 2 and 3A, the proximal portion 134 of the modified sleeve is provided with internal threads 136, which allow the modified sleeve to be coupled to the phacoemulsification hand piece 100 (FIG. 1). The distal portion 130 of the sleeve defines an irrigation conduit 132 through which fluid received from the first fluid conduit 114 can flow. At the distal end, or tip 152, two lateral holes 154, 156 are provided which permit fluid entering the modified sleeve from the first fluid conduit 114 to exit the irrigation conduit 132 both axially and radially.

Referring to FIGS. 2, 3B, and 3C, the balloon fluid conduit 138 extends along the longitudinal periphery of the sleeve 116. The distal end 142 of the balloon fluid conduit is coupled fluidtight to an open end 158 of the balloon 140. It will be appreciated that by forcing fluid, preferably a balanced saline solution or a viscoelastic material, e.g., Healon™ (made by Pharmacia), through the balloon fluid conduit, the balloon will swell. A portion of the balloon is further sealed to the tip 152 by gluing so that the entire balloon does not move away from the tip during swelling. As suggested by both FIGS. 2 and 3C, the balloon is thin (e.g., preferably 0.3 mm in width) when contracted 140 and swells considerably 140a (e.g., up to 5 mm in diameter) when filled with fluid.

Referring to FIGS. 2 and 3A, the proximal end 148 of the balloon fluid conduit 138 extends through a hole 146 in a lip 144 on the proximal portion 134 of the modified sleeve 116 and terminates in a female connector 150 for coupling with the tube 119 (shown in FIG. 1). Turning back to FIG. 1, the tube 119 is coupled to the syringe 117, which is of a type commonly known in the art such as a standard tuberculin 1 cc syringe. The syringe 117 can be easily manipulated to force fluid either proximally or distally through the tube 119 and the balloon fluid conduit 138 and thereby swell and contract the balloon 140, as desired. Preferably the syringe 117 is attached to the hand piece 100 in a position such that the syringe can be operated by the same hand of the practitioner that is holding the hand piece, i.e., the axis of the syringe is parallel to the axis of the hand piece and the nozzle of the syringe is directed toward the distal end of the hand piece. Alternatively, the syringe can be placed in any location and position that is comfortable to the practitioner, or may be left unattached from the hand piece so that the syringe may be operable by a second hand or by an assistant.

The phacoemulsification hand piece described above can perform a novel surgical procedure to remove cataracts. The sharp phaco needle 108 is first used to create a groove in the cataract, in a manner well known in the art. Once a groove has been carved into the cataract, the balloon at the distal end of the modified sleeve is moved into the groove and swelled. Swelling of the balloon fractures the cataract into halves or quarters. This process is termed herein as balloon nucleofractis. Consequently, each half or quarter can be similarly carved and fractured again using balloon nucleofractis. The smaller pieces can be easily removed using phacoemulsification in which the pieces are emulsified and aspirated through the phaco needle and through the aspiration tube. During aspiration, fluid also flows through the fluid tube to and through the irrigation conduit to irrigate the eye and maintain proper fluid pressure in the eye.

It will be appreciated that the phacoemulsification hand piece and the cataract removal procedure described above offer several advantages over currently utilized instruments and procedures. First, a single instrument can be used to carve a groove in the cataract, to break apart the cataract, and to aspirate the cataract rather quickly. There is no need for multiple instruments to be moved in and out of an incision in the eye which stresses the surgical site and further prolongs the surgical procedure. Second, breaking apart the cataract with a soft balloon is much safer than carving away the cataract with the phaco needle, as the sharp tip of the phaco needle is kept further from the delicate capsule of the lens. Third, the distal end of the instrument is sized to enter and exit through a small incision requiring no stitches at the completion of the procedure. Fourth, the balloon may be used to gently manipulate, move, and/or protect other delicate eye tissue during cataract removal.

Turning to FIGS. 4 through 5C, a second embodiment of a modified sleeve 216 for use with a balloon nucleofractis apparatus, substantially similar to the modified sleeve of the first embodiment (with similar parts having numbers incremented by 100), is shown. The modified sleeve 216 is a hollow tubular member generally having a distal portion 230, a proximal portion 234, a balloon fluid conduit 238, and a balloon 240.

Referring to FIGS. 4 and 5A, the proximal portion 234 of the sleeve is provided with a relatively thick wall 266 and internal threads 236. The internal threads 236 couple the modified sleeve 216 to a phacoemulsification hand piece. The thick wall 266 defines a proximal portion 248 of a balloon fluid conduit 238 and a female connector 250 for the balloon fluid conduit. The female connector 250 can couple the balloon fluid conduit 238 to a tube and a syringe, as in the first embodiment.

Referring to FIGS. 4 and 5B, the distal portion 230 of the sleeve defines an irrigation conduit 232 and a distal portion 243 of the balloon fluid conduit 238, such that the irrigation conduit and the distal portion of the balloon fluid conduit share a common wall 264. Referring to FIGS. 4 and 5C, the distal portion of the sleeve further defines two lateral holes 254, 256 at a tip 252 of the sleeve, thereby permitting fluid which enters the modified sleeve from a fluid tube (similar to the fluid tube 114 of the first embodiment) to exit the irrigation conduit 232 both axially and radially.

Still referring to FIGS. 4 and 5C, the balloon 240 is provided with an open end 258, which is coupled fluidtight to the distal end of the 242 of the balloon fluid conduit. It will be appreciated that the balloon 240 can be swelled 240a by forcing fluid through the balloon fluid conduit. A portion of the balloon is further glued to the tip 252 of the irrigation conduit so that the entire balloon does not move away from the tip 152 during swelling. The balloon is of dimensions as described in the first embodiment.

Turning to FIGS. 6 through 7C, a third embodiment of a modified sleeve 316 for use with a balloon nucleofractis apparatus, substantially similar to the modified sleeve of the first embodiment (with similar parts having numbers incremented by 200), is shown. The modified sleeve 316 is a hollow tubular member generally having a distal portion 330, a proximal portion 334, a balloon fluid conduit 338, and a balloon 340.

Referring to FIGS. 6 and 7A, the proximal portion 334 of the sleeve is provided with a female friction fitting 337. The female friction fitting 337 connects the modified sleeve 316 to a phacoemulsification hand piece having male friction fitting at a distal end (not shown).

Referring to FIGS. 6 and 7B, the distal portion 330 of the sleeve defines an irrigation conduit 332 and a distal portion 343 of the balloon fluid conduit 338, such that the irrigation conduit and the distal portion 343 of the balloon fluid conduit share a common wall 364. Referring to FIGS. 6 and 7C, the distal portion of the sleeve is further provided with a tip 352 and defines two lateral holes 354, 356 at a tip 352. The lateral holes permit fluid which enters the modified sleeve from a fluid conduit (similar to the fluid tube 114 of the first embodiment shown in FIG. 1) to exit the irrigation conduit 332 both axially and radially.

Still referring to FIGS. 6 and 7C, the balloon 340 is provided with an open end 358, which is coupled fluidtight to the distal end 342 of the balloon fluid conduit. It will be appreciated that by forcing fluid through the balloon fluid conduit the balloon 340 will swell to the size shown at 340a. A portion of the balloon is further glued to the tip 352 of the irrigation conduit so that the balloon does not move away from the tip 352 during swelling. The balloon is of similar dimensions as the balloon described in the first embodiment.

Turning back to FIGS. 6 and 7A, the proximal portion 348 of the balloon fluid conduit 338 extends through the interior of the proximal portion 334 of the sleeve such that the balloon fluid conduit and the proximal portion of the sleeve are separable, i.e., they do not share a common wall except at the juncture 349 of the proximal portion 334 of the sleeve and the distal portion 330 of the sleeve. A female connector 350 is provided at the proximal end 351 of the proximal portion 348 of the balloon fluid conduit. The female connector 350 can couple the balloon fluid conduit 338 to a fluid supply means. It will be appreciated that having a balloon fluid conduit 338 which extends through the interior of the proximal portion 334 of the sleeve permits connection to a fluid supply means located within the housing of a phacoemulsification hand piece.

Turning to FIG. 8, a fourth embodiment of a nucleofractis apparatus 400 is shown. The nucleofractis apparatus includes an ophthalmic hand piece 402 having a proximal end 404 and a distal end 406, a phaco needle 408 attached to the distal end 406, an external aspiration tube 412 and an external fluid tube 414. An irrigation sleeve 416 extends over the phaco needle 408 and is coupled to the distal end 406 of the tubular housing. A substantially rigid fracture lever 420 having a distal end 424 and a proximal actuator arm 422 terminating in a finger tab 423 is coupled to the irrigation sleeve 416 by a coupling band 426. The actuator arm and distal end of the fracture lever are preferably made of a thin metal or plastic. The coupling band 426 may be formed integral with the fracture lever 420 or may be a separate piece in the form of a strap or band coupled by gluing or heat sealing to the fracture lever 420 and designed to fit over the distal end of the irrigation sleeve. The fracture lever and coupling band are coupled to permit the fracture lever to move at a fulcrum point 428 such that the distal end 424 can move radially outward. Alternatively, the irrigation sleeve may be molded to integrally include the fracture lever.

Referring to FIGS. 8 and 9, in practice the phaco needle 408 is used to create a groove 430 in a cataract 432. The phaco needle 408 and the distal end 424 of the fracture lever are then inserted into the groove 430. When the practitioner presses the actuator arm 422 with a finger to move the actuator arm to a second position 422a, the distal end 424 moves radially outward to a second position 424a spreading the groove with the phaco needle and the distal end of the fracture lever, and thereby splitting the cataract.

Each of the above embodiments of a nucleofractis irrigation sleeve having a balloon or lever attached thereto can also be adapted for use with a YAG laser hand piece. The YAG laser hand piece appears generally similar to the phacoemulsification hand piece and is provided with an irrigation sleeve. However, the YAG laser hand piece utilizes a YAG laser tip instead of a phaco needle to carve a groove in the cataract and to emulsify a partially fractured cataract. As the YAG laser hand piece operates in a similar manner in other respects, i.e., having aspiration and irrigation means which operate through a removably couplable irrigation sleeve, it is clear that the above described modified irrigation sleeve would have application therefor.

Turning now to FIG. 10, a fifth embodiment of a nucleofractis apparatus 500 is shown. The apparatus 500 includes a proximal syringe 510 coupled fluidtight to a distal balloon 512. The syringe includes a tubular member 514, a plunger 516 and a nozzle 518. Located within the tubular member is a fluid 520, e.g., a balanced saline solution or a viscoelastic material. As the plunger 516a is moved distally, the fluid moves into the balloon and swells the balloon 512a. The distal balloon can be introduced into the eye through the same incision used for the insertion of other instruments in the cataract removal procedure or may be inserted through a separate side incision.

While each of the prior embodiments are preferable in a majority of circumstances in that each provides a single apparatus operable by a single hand of a practitioner and is insertable into a single incision in the eye which can fracture a cataract, it will nevertheless be appreciated that under certain circumstances it may be desirable to use the balloon nucleofractis apparatus of the fifth embodiment as it can be operated by a practitioner's assistant or as it may provide benefit to the practitioner during certain procedures.

There have been described and illustrated herein several embodiments of a ophthalmic hand piece having a modified sleeve and a method of performing a cataract removal procedure. While particular embodiments of the invention have been described, it is not intended that the invention be limited thereto, as it is intended that the invention be as broad in scope as the art will allow and that the specification be read likewise. Thus, while the fluid tube and aspiration tube are shown attached to the exterior of the housing of an ophthalmic instrument hand piece, it will be appreciated that the tubes may also extend through the interior of the housing. Furthermore, while the balloon fluid conduit has been shown to be injection molded with the modified sleeve, it will be appreciated that a separable balloon fluid conduit may also be coupled to the exterior of the modified sleeve by gluing, heat sealing, suturing or other means, such that it operates in a similar manner. In addition, while the balloon fluid conduit has been shown to extend lengthwise along the periphery of the sleeve, it will be appreciated that the balloon fluid conduit may extend along a more circuitous path from the proximal end of the sleeve to the peripheral end of the sleeve. Also, while threads and friction fittings are disclosed for coupling the modified sleeve to the tubular housing, it will be appreciated that other coupling means, e.g., Luer fittings, can be used as well. Furthermore, while a syringe is disclosed as a fluid supply means, it will be recognized that other fluid supply means can be used. Moreover, while a saline solution and a viscoelastic solution have been disclosed as fluids for swelling the balloon, it will be appreciated that other fluids, including air, can be used as well. In addition, while the balloon is disclosed as being sealed to the tip by gluing, it will be appreciated that the balloon may be otherwise sealed to the tip, for example, by heat sealing, suturing, or injection molding. Also, while the syringe is disclosed as being strapped to the tubular housing, it will be appreciated that the syringe may be attached to the housing by other means and/or separable. For example, the syringe may be glued, taped, coupled by Velcro™, or coupled to a mounting. Furthermore, the balloon fluid conduit may extend substantially beyond the proximal end of the irrigation sleeve and have a coupling means located at its proximal end, i.e., it can be coupled directly to a fluid supply means without the use of a separable tube. Moreover, while a YAG laser is preferred when a laser is used, it will be appreciated that other lasers can also be used. Likewise, while a single mechanical spreader in the form of a lever was disclosed, it will be appreciated that other mechanical means, both flexible and rigid could be utilized. It will therefore be appreciated by those skilled in the art that yet other modifications could be made to the provided invention without deviating from its spirit and scope as so claimed.

I claim:

1. A nucleofractis irrigation sleeve for use with an ophthalmic hand piece during cataract eye surgery, said nucleofractis irrigation sleeve, comprising:
   a) a tubular member carrying an irrigation conduit and having a longitudinal axis, a first distal portion and a first proximal portion, said first proximal portion provided with a coupling means for coupling said tubular member to the ophthalmic hand piece; and
   b) a spreading means coupled to said tubular member for contacting a cataract, said spreading means having a proximal actuation portion and a distal portion, said distal portion adapted to extend away from said longitudinal axis upon actuating said proximal actuation portion.

2. A nucleofractis irrigation sleeve according to claim 1, wherein:
   said distal portion includes a balloon coupled adjacent to said distal portion of said tubular member, and said proximal actuation portion includes a balloon fluid conduit coupled substantially fluidtight to said balloon, said balloon adapted to swell and thereby extend away from said longitudinal axis when fluid is forced through said balloon fluid conduit and into said balloon.

3. A nucleofractis irrigation sleeve according to claim 2, wherein:
   said proximal actuation portion further includes a fluid supply means coupled to said balloon fluid conduit for forcing fluid through said balloon fluid conduit.

4. A nucleofractis irrigation sleeve according to claim 2, wherein:

said tubular member and said balloon fluid conduit are injection molded as an integral unit.

5. A nucleofractis irrigation sleeve according to claim 2, wherein:

said irrigation sleeve is made from an elastic silicone material.

6. A nucleofractis irrigation sleeve according to claim 2, wherein:

said balloon is adapted to swell to approximately 5 mm in diameter.

7. A nucleofractis irrigation sleeve according to claim 2, wherein:

said balloon is approximately 0.3 mm in width when not swelled.

8. A nucleofractis irrigation sleeve according to claim 2, wherein:

said tubular member defines a periphery and said balloon fluid conduit extends along said periphery.

9. A nucleofractis irrigation sleeve according to claim 2, wherein:

said tubular member is provided with a proximal wall and said balloon fluid conduit is provided with a second proximal portion, wherein said proximal wall of said tubular member defines said second proximal portion of said balloon fluid conduit.

10. A nucleofractis irrigation sleeve according to claim 2, wherein:

said balloon fluid conduit is provided with a second proximal portion and a second distal portion, wherein said second proximal portion of said balloon fluid conduit extends through said first proximal portion of said tubular member and said second distal portion of said balloon fluid conduit extends along said first distal portion of said tubular member.

11. A nucleofractis irrigation sleeve according to claim 1, wherein:

said spreading means has a distal end portion and a proximal actuator arm portion, and is adapted such that when said when said proximal actuator arm is actuated said distal end moves radially outward away from said longitudinal axis.

12. A nucleofractis ophthalmic instrument for use in cataract eye surgery, comprising:

a) a tubular housing member having a proximal end, a distal end, and a longitudinal axis;

b) an aspiration conduit coupled to said distal end of said housing member;

c) a nucleofractis irrigation sleeve having a tubular member, a spreading means for contacting a cataract, and a coupling means for coupling said tubular member to said distal end of said housing member;

d) an aspiration means coupled to said aspiration conduit for aspirating through said aspiration conduit; and e) an irrigation means coupled to said irrigation conduit for irrigating fluid through said irrigation conduit.

13. A nucleofractis ophthalmic instrument according to claim 12, wherein:

said tubular member of said nucleofractis irrigation sleeve has a first distal portion and said spreading means of said nucleofractis irrigation sleeve includes a balloon coupled adjacent to said first distal portion of said tubular member and a balloon fluid conduit coupled substantially fluidtight to said balloon, said balloon adapted to swell when fluid is forced through said balloon fluid conduit into said balloon.

14. A nucleofractis ophthalmic instrument according to claim 13, wherein:

said spreading means further includes a fluid supply means coupled to said balloon fluid conduit for forcing fluid through said balloon fluid conduit.

15. A nucleofractis ophthalmic instrument according to claim 13, wherein:

said balloon fluid conduit and said tubular member of said nucleofractis irrigation sleeve are injection molded as an integral unit.

16. A nucleofractis ophthalmic instrument according to claim 13, wherein:

said irrigation sleeve is made from an elastic silicone material.

17. A nucleofractis ophthalmic instrument according to claim 13, wherein:

said balloon is adapted to swell to approximately 5 mm in diameter.

18. A nucleofractis ophthalmic instrument according to claim 13, wherein:

said balloon is approximately 0.3 mm in width when not swelled.

19. A nucleofractis ophthalmic instrument according to claim 13, wherein:

said tubular member defines a periphery and said balloon fluid conduit extends along said periphery.

20. A nucleofractis ophthalmic instrument according to claim 13, wherein:

said tubular member is provided with a proximal wall and said balloon fluid conduit is provided with a proximal portion, wherein said proximal wall of said tubular member defines said proximal portion of said balloon fluid conduit.

21. A nucleofractis ophthalmic instrument according to claim 13, wherein:

said tubular member is further provided with a first proximal portion and said balloon fluid conduit is provided with a second proximal portion and a second distal portion, wherein said second proximal portion of said balloon fluid conduit extends through said first proximal portion of said tubular member and said second distal portion of said balloon fluid conduit extends along said first distal portion of said tubular member.

22. A nucleofractis ophthalmic instrument according to claim 12, wherein:

said spreading means of said nucleofractis irrigation sleeve includes a distal end and a proximal actuator arm, and is adapted such that when said when said proximal actuator arm is actuated said distal end moves radially outward away from said longitudinal axis.

23. A nucleofractis ophthalmic instrument according to claim 12, wherein:

said tubular housing member includes a phaco needle provided with a sharp tip.

24. A nucleofractis ophthalmic instrument according to claim 12, wherein:

said tubular housing member includes a laser.

25. A method of fracturing a cataract into at least two pieces using an ophthalmic hand piece and a balloon nucleofractis device carrying a swellable soft balloon, said method comprising:

a) creating a groove in the cataract using the ophthalmic hand piece;

b) positioning said balloon in said groove; and c) swelling said balloon positioned in said groove to fracture the cataract into at least two pieces.

26. A method of fracturing a cataract according to claim 25, further comprising:

d) prior to creating a groove, providing an incision in the lens of the eye;

e) after swelling the balloon, emulsifying at least one of said two pieces of the cataract such that an emulsion is formed;

f) irrigating fluid through said irrigation conduit and into the eye; and g) aspirating said emulsion from the eye through said aspiration conduit.

27. A method of performing surgery on an eye having a cataract to remove the cataract, said method using an ophthalmic hand piece having means to create a groove in a cataract, means for emulsification, and means for spreading the groove, said method comprising:

a) creating a groove in the cataract;

b) positioning said means for spreading the groove in said groove; and c) actuating said means for spreading the groove to fracture the cataract into at least two pieces.

28. A method of performing surgery on an eye having a cataract to remove the cataract according to claim 27, further comprising:

d) prior to creating the groove, providing an incision in the lens of the eye;

e) after actuating said for means for spreading the groove, emulsifying at least one of said two pieces of the cataract such that an emulsion is formed;

f) irrigating fluid through said irrigation conduit and into the eye; and g) aspirating said emulsion from the eye through said aspiration conduit.

\* \* \* \* \*